(12) United States Patent
Wiesent

(10) Patent No.: US 10,605,729 B2
(45) Date of Patent: Mar. 31, 2020

(54) ATR-SPECTROMETER

(71) Applicant: Spectrolytic GmbH, Wernberg-Koeblitz (DE)

(72) Inventor: Benjamin Wiesent, Wernberg-Koeblitz (DE)

(73) Assignee: Spectrolytic GmbH, Wermberg-Koeblitz (DE)

( * ) Notice: Subject to any disclaimer, the term of this patent is extended or adjusted under 35 U.S.C. 154(b) by 0 days.

(21) Appl. No.: 16/252,625

(22) Filed: Jan. 19, 2019

(65) Prior Publication Data

US 2019/0154577 A1    May 23, 2019

Related U.S. Application Data

(63) Continuation of application No. PCT/EP2017/067937, filed on Jul. 14, 2017.

(30) Foreign Application Priority Data

Jul. 20, 2016  (DE) ........................ 10 2016 008 886

(51) Int. Cl.
*G01N 21/552* (2014.01)
*G01J 3/36* (2006.01)
(Continued)

(52) U.S. Cl.
CPC ............ *G01N 21/552* (2013.01); *G01J 3/10* (2013.01); *G01J 3/36* (2013.01); *G01N 21/35* (2013.01);
(Continued)

(58) Field of Classification Search
CPC ................ G01N 21/552; G01N 21/35; G01N 2201/0635; G01N 2201/0636;
(Continued)

(56) References Cited

U.S. PATENT DOCUMENTS 4,730,882 A * 3/1988 Messerschmidt ........ G02B 6/10
356/300
5,616,922 A * 4/1997 Reffner .................. G01N 21/09
250/339.11

(Continued)

FOREIGN PATENT DOCUMENTS

DE    102006036409 A1    10/2007
DE    102007058611 A1    6/2009

OTHER PUBLICATIONS

International Search Report of the European Patent Office in PCT/EP2017/067937 (from which this application claims priority) dated Oct. 20, 2017 and English-language translation thereof.

*Primary Examiner* — Roy M Punnoose
(74) *Attorney, Agent, or Firm* — Falk Ewers; Ewers IP Law PLLC

(57) ABSTRACT

An ATR-spectrometer has an ATR-crystal which includes a truncated conical section and two planar surfaces that are arranged in parallel to each other, an emitter configured to emit electromagnetic radiation via one of the surfaces to a lateral surface of the truncated conical section configured to reflect the electromagnetic radiation to propagate in the ATR-crystal by a plurality of reflections and to subsequently couple out of the ATR-crystal, and a detector configured to detect the electromagnetic radiation coupled out. The one of the surfaces includes an in-coupling region for coupling in the electromagnetic radiation. The in-coupling region is a projection of a circumferentially extending section of the lateral surface to the one of the surfaces. The emitter has an electromagnetic radiation emitting surface, the projection of which on the in-coupling region exceeds, seen from a center point of the one of the surfaces, an angle (α) of at least 1.5°.

21 Claims, 3 Drawing Sheets

(51) Int. Cl.
*G01J 3/10* (2006.01)
*G01N 21/35* (2014.01)

(52) U.S. Cl.
CPC ............... *G01J 2003/102* (2013.01); *G01N 2201/0635* (2013.01); *G01N 2201/0636* (2013.01); *G01N 2201/0638* (2013.01)

(58) Field of Classification Search
CPC ...... G01N 2201/0638; G01J 3/10; G01J 3/36; G01J 2003/102
USPC ........................................................ 356/445
See application file for complete search history.

(56) References Cited

U.S. PATENT DOCUMENTS

| | | | | |
|---|---|---|---|---|
| 5,942,754 | A * | 8/1999 | Yamaguchi | G01N 21/552 |
| | | | | 250/339.11 |
| 5,965,889 | A * | 10/1999 | Brierley | G01J 3/45 |
| | | | | 250/339.11 |
| 6,118,520 | A | 9/2000 | Harner | |
| 6,420,708 | B2 * | 7/2002 | Wilks, Jr. | G01N 21/35 |
| | | | | 250/339.07 |
| 2008/0309922 | A1 | 12/2008 | Anders et al. | |
| 2010/0303413 | A1 | 12/2010 | Mikkelsen et al. | |
| 2012/0293860 | A1 * | 11/2012 | Gundlach | G01N 21/552 |
| | | | | 359/351 |
| 2016/0299063 | A1 * | 10/2016 | Ebisawa | G01N 21/3577 |

* cited by examiner

ATR-SPECTROMETER

CROSS REFERENCE TO RELATED APPLICATIONS

This application is a continuation application of international patent application PCT/EP2017/067937, filed on Jul. 14, 2017, designating the United States and claiming priority to German application 10 2016 008 886.9, filed on Jul. 20, 2016, and the entire content of both applications is incorporated herein by reference.

TECHNICAL FIELD

The invention relates to an ATR-spectrometer.

BACKGROUND

An attenuated total reflection (ATR)-spectrometer includes a rectangular ATR-crystal that is in contact with a sample to measure a spectrum of the sample. Light is coupled into an end of the ATR-crystal to measure the spectrum. The light propagates by multiple total internal reflections from one end to another end of the ATR-crystal and exits the ATR-crystal there. Due to the total internal reflection, evanescent waves are formed in the sample, wherein an interaction of the evanescent waves with the sample takes place. This interaction leads to a spectrum of the exiting light, wherein the spectrum is characteristic for the sample.

It is disadvantageous that the ATR-crystal is cost-intensive in its production. In addition, the production for a holder for mounting the ATR-crystal in the ATR-spectrometer is cost-intensive. Furthermore, the ATR-crystal has only a small in-coupling surface for coupling the light in the ATR-crystal and a small outcoupling surface for coupling the light out of the ATR-crystal, so that only a small number of light sources and detectors can be provided.

Conventionally, the dimensions of the detectors are in the magnitude of the width of the intensity distributions of the light exiting the ATR-crystal. The intensity distributions conventionally have a Gauss shape with steep gradients. However, this is disadvantageous, since an amount of light that can be measured by the detectors and therefore also the signal-to-noise ratio of the measured spectra strongly depend on the positioning of the detectors. In the case that a calibration of the ATR-spectrometer is carried out, the calibration depends on the amount of light impinging on the detectors. Therefore, the accuracy of the calibration also strongly depends on the positioning of the detectors. A different thermal expansion of the ATR-crystal and of a circuit board, on which the light sources and the detectors are arranged, can possibly lead to a negative impact on the calibration.

SUMMARY

It is therefore an object of the invention to provide an ATR-spectrometer, with which the problems mentioned before can be solved.

The ATR-spectrometer according to an aspect of the invention includes an ATR-crystal that includes a truncated conical section and two planar surfaces that are arranged parallel with respect to each other, an emitter that is configured to emit electromagnetic radiation via one of the surfaces and essentially perpendicular to the one of the surfaces to a lateral surface of the truncated conical section. The lateral surface is configured to reflect the electromagnetic radiation to the one of the surfaces so that the electromagnetic radiation can be propagated in the ATR-crystal by multiple reflections on the two surfaces and can be subsequently coupled out of the ATR-crystal by a reflection on the lateral surface of the truncated conical section. The ATR-spectrometer further includes a detector that is configured to detect the electromagnetic radiation that is coupled out. One of the surfaces includes an in-coupling region for coupling in the electromagnetic radiation. The in-coupling region is a projection of a circumferentially extending section of the lateral surface to the one of the surfaces. The emitter has an electromagnetic radiation emitting surface, which projection on the in-coupling region exceeds, seen from a center point of the one of the surfaces, an angle of at least 1.5°.

The emitter optionally includes beam shaping elements, for example a lens and/or a concave mirror, and the electromagnetic radiation emitting surface of the emitter is where the electromagnetic radiation exits the emitter. It was found that due to the ATR-crystal with the truncated conical section and the projection of the electromagnetic radiation emitting surface on the one of the surfaces with the angle exceeding at least 1.5°, an intensity distribution of the electromagnetic radiation entering the ATR-crystal exits the ATR-crystal again strongly widened after its propagation through the ATR-crystal. Surprisingly, this exiting intensity distribution has central in circumferential direction of the ATR-crystal a broad plateau, in which the intensity has a maximum and is essentially constant. This plateau is advantageous, since the signal-to-noise ratio of the measured spectra and the calibration of the ATR-spectrometer do then not strongly depend on the positioning of the detectors. A positioning of the detectors in a region of the plateau is therefore particularly advantageous with respect to the signal-to-noise ratio and the calibration. On the other hand, in case the angle is smaller than 1.5°, the electromagnetic radiation exiting the ATR-crystal forms intensity maxima with small dimensions and steep gradients. A positioning of the detectors in the region of the intensity maxima leads disadvantageously to a strong sensitivity of the calibration with respect to the positioning.

Furthermore, a higher number of the emitters and the detectors can be provided on the ATR-crystal by providing the truncated conical section with its lateral surface as it is possible in the case of the conventional rectangular ATR-crystal. It is thereby possible to measure the spectra with a higher spectral resolution and/or the spectra can be measured in a broader wavelength range as it is the case for conventional rectangular ATR-crystal.

According to an aspect of the invention, the projection of the electromagnetic radiation emitting surface on the in-coupling region exceeds the angle of at least 8°. A particular broad and smooth plateau can therefore be obtained.

According to another aspect of the invention, the emitter is configured to illuminate a region of the base surface of the truncated conical section, wherein the region has an extension in a circumferential direction of the ATR-crystal, which is longer than an extension of the electromagnetic radiation emitting region of the emitter in the circumferential direction. It was found that a plateau with a particular uniform intensity is generated with such an illumination of the base surface.

According to a further aspect of the invention, the emitter is configured to emit the electromagnetic radiation with a divergence angle from 90° to substantially 180°, in particular from 150° to substantially 180°. A particular broad plateau of the exiting radiation can be obtained due to this large divergence angle. Furthermore, the plateau is particularly smooth due to the large divergence angle. An extension of the base surface of the truncated conical section in a direction in which the electromagnetic radiation propagates in the ATR-crystal is typically at least 2.5 cm, in particular at least 4 cm. A particular broad and smooth plateau can therefore be obtained.

According to an aspect of the invention, the projection of the electromagnetic radiation emitting surface of the emitter on the in-coupling region covers at least 25%, in particular 100%, of a ring width of the in-coupling region. A particular large amount of the electromagnetic region can thereby be coupled in the ATR-crystal. Furthermore, the plateau has a particular long extension in radial direction of the ATR-crystal.

According to an aspect of the invention, the width of the in-coupling region in a radial direction of the ATR-crystal is from 0.25 mm to 5 mm. The distance from the emitter to the lateral surface is typically from 0.5 mm to 7 mm. Due to the short distance, it is advantageously caused that a large amount of the electromagnetic radiation is coupled in the ATR-crystal. According to another aspect of the invention, the lateral surface and the base surface of the truncated conical section enclose an angle from 15° to 60°.

According to yet another aspect of the invention, the truncated conical section is circular conical truncated. This can be advantageously easily produced by a turning method, in which the truncated conical section is produced out of a workpiece by grinding, whereby the ATR-crystal is less cost-intensive than the conventional rectangular ATR-crystal. The normals of the two surfaces are typically parallel to a cone axis of the truncated conical section. Also, this geometry can be produced advantageously easy by the turning method, whereby the ATR-crystal is advantageously less cost-intensive than the conventional rectangular ATR-crystal. In addition, a more cost-efficient holder for mounting the ATR-crystal in the ATR-spectrometer can be produced for this geometry than it is the case for the conventional rectangular ATR-crystal.

According to an aspect of the invention, the ATR-crystal includes a cylindrical section which circular surfaces have the same diameter as the base surface of the truncated conical section, and the base surface of the truncated conical section coincides with one of the circular surfaces of the cylindrical section so that the other of the circular surfaces of the cylindrical section and the top surface of the truncated conical section form two parallel surfaces. Also, this geometry having the cylindrical section can be advantageously easily produced by the turning method, whereby the ATR-crystal is less cost-intensive than the conventional rectangular ATR-crystal. Furthermore, a breaking of the ATR-crystal in the region of the lateral surface is unlikely due to this geometry.

According to an aspect of the invention, the electromagnetic radiation is infrared light, the ATR-crystal is transparent for the infrared light and the detector is configured to detect the infrared light. The ATR-crystal typically includes zinc sulphide, zinc selenide, germanium, calcium fluoride, barium fluoride, thallium bromide iodide, silicon, AMTIR, sapphire and/or diamond. The ATR-crystal particularly typically consists of one of the substances mentioned before.

The ATR-spectrometer typically includes a wavelength selective element that is arranged such that the electromagnetic radiation that is coupled out can be guided through the wavelength selective element before the electromagnetic radiation impinges on the detector. According to an aspect of the invention, the wavelength selective element is a prism, an optical grating, at least one bandpass filter and/or a linear variable filter, in particular a linear variable band pass filter and/or a linear variable edge filter.

The ATR-spectrometer typically includes a plurality of arrangements out of the emitter, the detector and the wavelength selective element, wherein the arrangements are arranged next to each other in circumferential direction of the ATR-crystal, the emitters are in particular configured to emit different spectra and the wavelength selective elements are in particular configured to select different wavelengths. The emitters and the detectors are typically arranged alternatingly in the circumferential direction of the ATR-crystal. A cross talk between the different arrangements is advantageously reduced to the alternating arrangement. In addition, the heat input from the emitters in the ATR-crystal is mostly symmetric due to the alternating arrangement, whereby mechanical tensions in the ATR-crystal can be reduced. In case mechanical tensions occur in the ATR-crystal, these can lead to asymmetries in the ATR-crystal. The asymmetries can have a negative impact on the measured spectra. This negative impact can be advantageously compensated by measuring a spectrum by each of the arrangements and by subsequently averaging the spectra.

According to an aspect off the invention, the detector includes a plurality of sensors that are configured to detect the radiation emitted by a single one of the emitters. It is thereby possible to calibrate only one of the sensors and to use the so obtained calibration function for the other sensors. By calibrating only one of the sensors, the method for calibrating is advantageously easy and little cost-intensive.

A photoactive surface of the detector typically has an extension in circumferential detection of the ATR-crystal that is shorter than an extension of a plateau, wherein the extension of the plateau is extending in the circumferential direction, wherein the plateau is a region of the electromagnetic radiation that is coupled out of the ATR-crystal, wherein in the region an intensity distribution of the electromagnetic radiation that is coupled out of the ATR-crystal reaches a maximum and is substantially constant. The measured spectra are thereby advantageously mostly independent on possibly occurring heat expansions in the ATR-spectrometer.

BRIEF DESCRIPTION OF THE DRAWINGS

The invention will now be described with reference to the drawings wherein.

DESCRIPTION OF EXEMPLARY EMBODIMENTS

Figure 1:
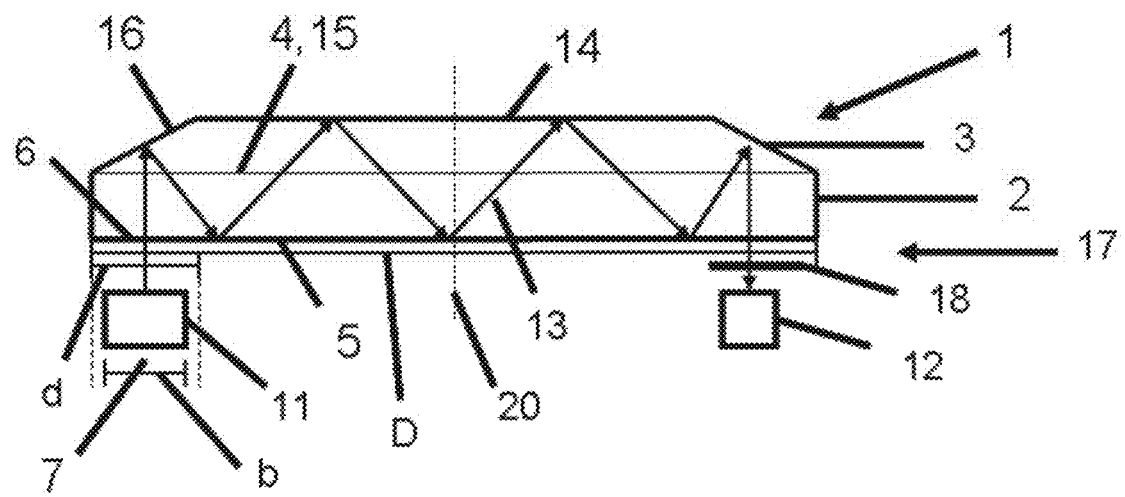
FIG. 1 shows a side view of the ATR-spectrometer according to an exemplary embodiment of the invention.
Figure 2:
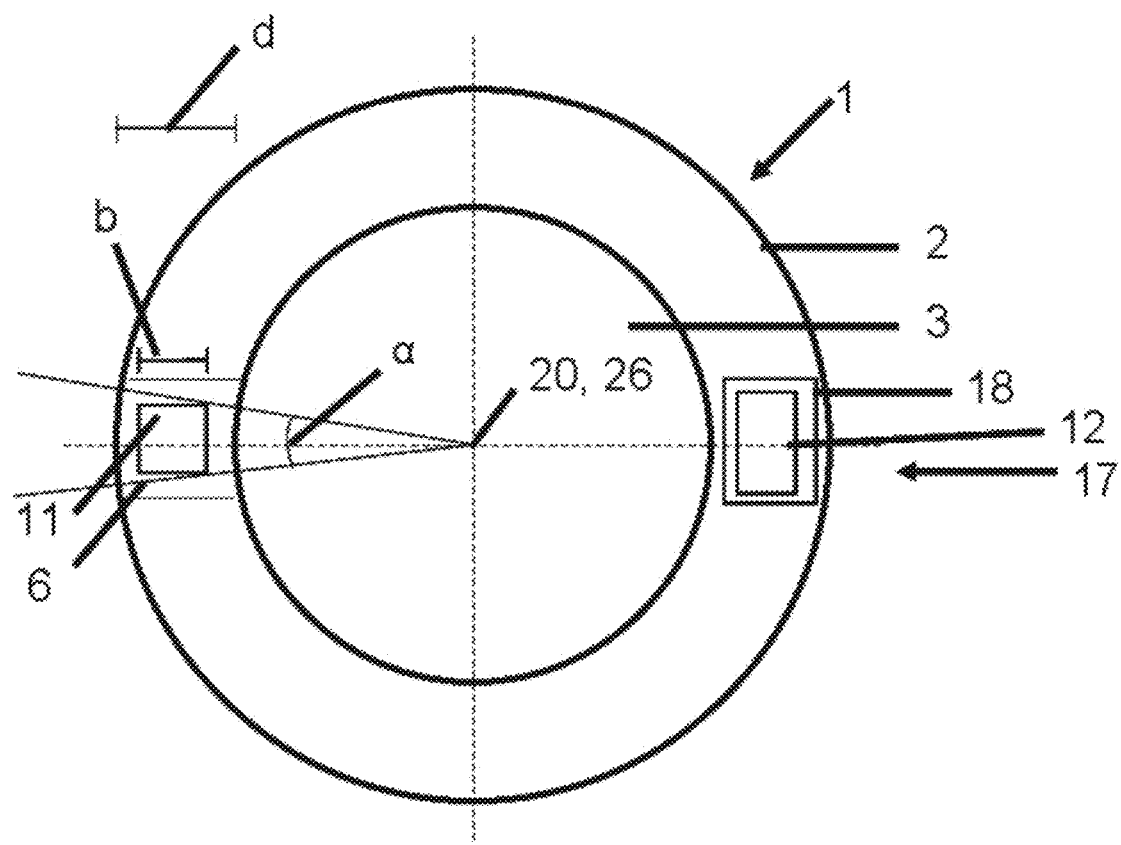
FIG. 2 shows a top view of the ATR-spectrometer.

As shown in FIGS. 1 and 2, an ATR-spectrometer 17 includes an ATR-crystal 1, an emitter 11, a detector 12 and a wavelength selective element 18. The ATR-crystal 1 includes a cylindrical section 2 and a truncated circular conical section 3 with an exposed lateral surface 16. The two circular surfaces 4, 5 of the cylindrical section 2 have the same diameter as the base surface 15 of the truncated circular conical section 3. One of the two circular surfaces 4 of the cylindrical section 2 coincides with the base surface 15 of the truncated circular conical section 3, so that the other of the two circular surfaces 5 of the cylindrical section 2 and the top surface 14 of the truncated circular conical section 3 form two parallel and exposed surfaces. The normals of the two surfaces are parallel to the cone axis 20 of the truncated circular conical section 3. The extension D of the base surface 15 of the truncated circular conical section 3 in the direction, in which the electromagnetic radiation 13 propagates in the ATR-crystal 1, i.e., the diameter of the base surface 15, is for example at least 2.5 cm, in particular at least 4 cm.

The ATR-crystal 1 is in particular transparent for infrared light. The ATR-crystal 1 can comprise zinc sulphide, zinc selenide, germanium, calcium fluoride, barium fluoride, thallium bromide iodide, silicon, AMTIR, sapphire and/or diamond. The ATR-crystal 1 can in particular consist of one of the substances mentioned before.

The emitter 11 is configured to emit the electromagnetic radiation 13, in particular the infrared light, via one of the surfaces and substantially perpendicular to the one surface to the lateral surface 16 of the truncated conical section 3. The lateral surface 16 is configured to reflect the electromagnetic radiation 13 to the one of the surface, so that the electromagnetic radiation 13 can be propagated in the ATR-crystal 1 by multiple reflections on the surfaces. The electromagnetic radiation 13 can subsequently be coupled out of the ATR-crystal 1 by a reflection on the lateral surface 16 of the truncated conical section 3.

The one surface includes an in-coupling region 6 for coupling in the electromagnetic radiation 13, wherein the in-coupling region 6 is the projection of a circumferentially extending section of the lateral surface 16 on the one of the surfaces. The emitter 11 has an electromagnetic radiation emitting surface, which projection on the in-coupling region 6 exceeds, seen from a center point 26 of the one of the surface, an angle α of at least 1.5°, in particular at least 8°. Therefore, the emitter 11 is arranged in a spatial region 7 that has the shape of a section of an annular gap that extends from the in-coupling region 6 away from the in-coupling region 6. The spatial region 7 is in FIG. 1 the region that extends between the two dashed lines. The emitter 11 can optionally include beam shaping elements, for example a lens and/or a concave mirror, and the electromagnetic radiation emitting surface is the region of the emitter 11, where the electromagnetic radiation 13 exits the emitter 11. The emitter 11 is configured to emit the electromagnetic radiation 13 with a divergence angle from 90° to substantially 180°, in particular from 150° to substantially 180°. The projection of the electromagnetic radiation emitting surface of the emitter 11 on the in-coupling region 6 covers at least 25%, in particular 100%, of the ring width d of the in-coupling region 6.

The emitter 11 can be configured to illuminate a region of the base surface 15 of the truncated conical section 3, wherein the region has an extension in a circumferential direction of the ATR-crystal 1, which is longer than an extension of the electromagnetic radiation emitting region and in the spatial region 7 arranged region of the emitter 11 in the circumferential direction.

The detector 12 is configured to detect the electromagnetic radiation 13 that is coupled out. The detector 12 is in particular configured to detect the infrared light. The wavelength selective element 18 is arranged such that the electromagnetic radiation 13 that is coupled out can be guided through the wavelength selective element 18 before it impinges on the detector 12. The wavelength selective element 18 can be a prism, an optical grating, at least one bandpass filter and/or linear variable filter, in particular a linear variable band pass filter and/or a linear variable edge filter.

A sample is contacted with at least one of the two surfaces for measuring a spectrum of the sample. The material of the ATR-crystal is to be chosen such that the refractive index $n_1$ of the material is higher than refractive index $n_0$ of the sample, so that total internal reflection can occur. Furthermore, an angle is to be chosen to be larger than a threshold angle β, wherein the angle is the angle that the electromagnetic radiation 13 encloses during the multiple reflections with the normal of the two surfaces and wherein β=arcsin $(n_0/n_1)$. The angle can be set by the inclination of the lateral surface 16, i.e., an angle that the lateral surface 16 and the base surface 15 of the truncated conical section 3 enclose is from 15° to 60°.

Figure 3:
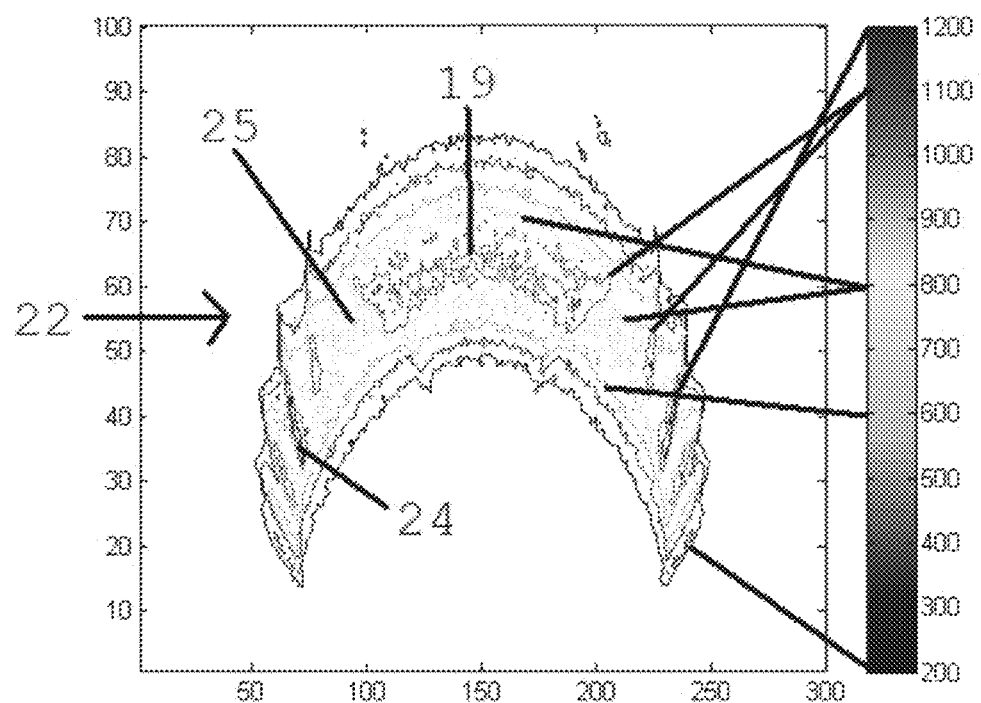
FIG. 3 shows a two-dimensional intensity distribution of electromagnetic radiation exiting an ATR-crystal of an ATR-spectrometer having a short emitter.
Figure 4:
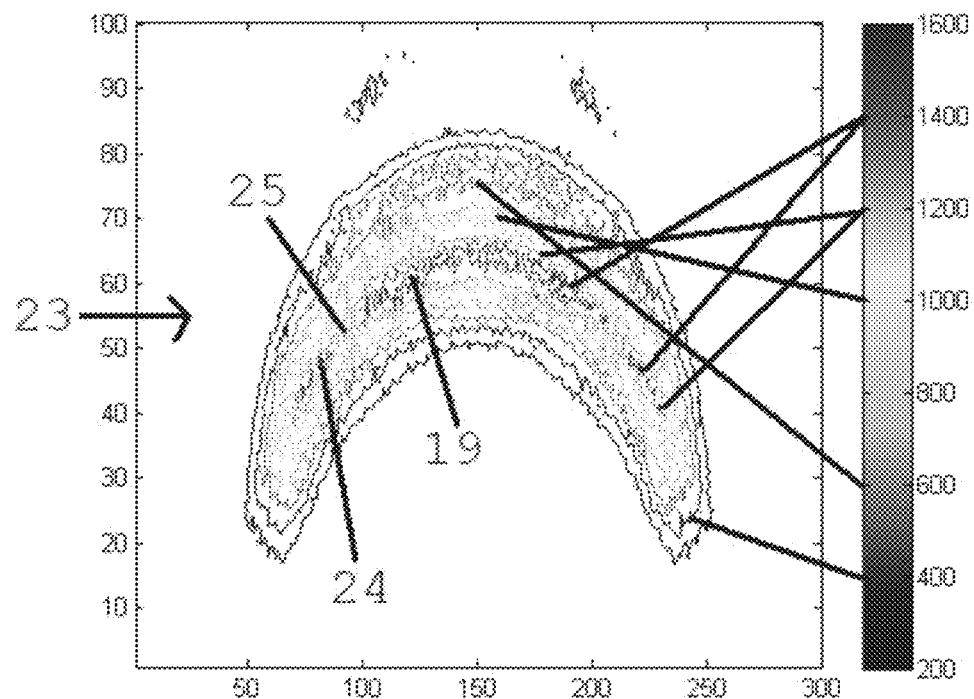
FIG. 4 shows a two-dimensional intensity distribution of electromagnetic radiation exiting the ATR-crystal of the ATR-spectrometer according to an exemplary embodiment of the invention.

FIG. 3 shows a two-dimensional intensity distribution 22 of electromechanical radiation that exits an ATR-crystal 1 of an ATR-spectrometer that does not belong to the invention. FIG. 4 shows an intensity distribution 23 that is comparable to FIG. 3, wherein the intensity distribution 23 belongs to the ATR-spectrometer 1 according to FIGS. 1 and 2. The intensity distributions 22, 23 were determined by a simulation by a commercially available simulation software. The ATR-spectrometer that does not belong to the invention differs from the ATR-spectrometer 1 according to FIGS. 1 and 2, in that the projection of the electromagnetic radiation emitting surface on the in-coupling region has, seen from a center point of the one of the surface, an angle that is substantially smaller than 1.5°.

As it can be seen from FIGS. 3 and 4, the intensity distributions 22, 23 include a plateau 19 central in circumferential direction of the ATR-crystal 1, wherein the intensity distribution is substantially constant in the plateau 19. The plateau 19 is characterized in that in the region of the plateau 19 the intensity deviates from an average value of the plateau 19 by a maximum of 5%. Intensity maxima 24 are arranged in both circumferential directions therefrom. Intensity minima 25 are arranged between the intensity maxima 24 and the plateau 19, wherein the intensity minima 25 are saddle points of the respective intensity distribution 22, 23. As it can be seen in FIG. 3, the intensity distribution 22 is inhomogeneous, with several intensity maxima 24 having a high contrast. To the contrary, the plateau 19 of the intensity distribution 23 is smoother than the plateau 19 of the intensity distribution 22 and the intensity maxima 24 of the intensity distribution 23 have a lower contrast than the intensity maxima 24 of the intensity distribution 22. The arrangement of the detector 12 of the ATR-spectrometer according to the exemplary embodiment of the invention is thereby less sensitive with respective to the positioning than of the ATR-spectrometer according to FIG. 3.

Figure 5:
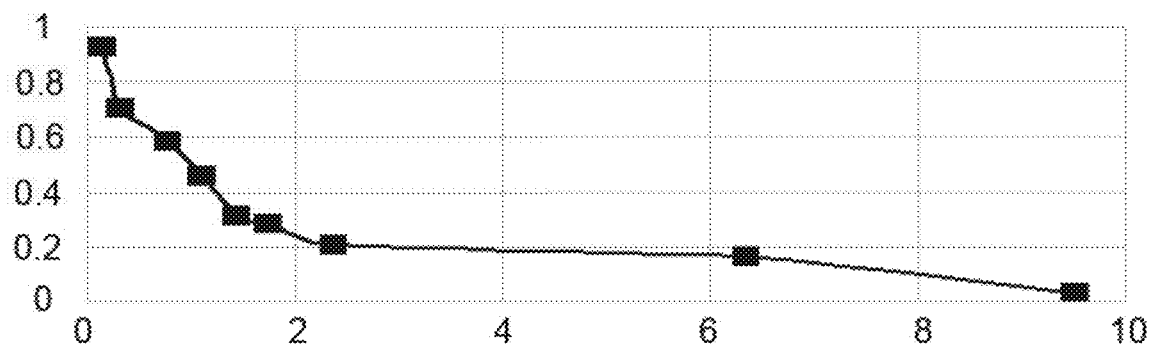
FIG. 5 shows a plot of a respective contrast parameter of different intensity distributions depending on an angle.

FIG. 5 shows a plot, wherein for making of the plot the length of the electromagnetic radiation 13 emitting surface of the emitter 11 in circumferential direction of the ATR-crystal 1 was systematically varied in the simulation, the length of the electromagnetic radiation 13 emitting surface in radial direction of the ATR-crystal remained identical. The angle of the projection of the electromagnetic radiation 13 emitting surface on the in-coupling region 6, as seen from the center point 26, is plotted in ° (degree) over the horizontal axis. A contrast parameter K of the two-dimensional intensity distribution resulting from the respective simulation is plotted over the vertical axis. The contrast parameter is thereby defined by K=[I(maximum)−I(minimum)]/I(plateau), wherein I(maximum) is the intensity maximum 24 of the intensity distribution, I(minimum) is the intensity minimum 25 between the intensity maximum 24 and the plateau 19, wherein the intensity minimum 25 is a saddle point in the two two-dimensional intensity distribution, and I(plateau) is the intensity of the plateau 19. An averaging of the intensities in the plateau 19 was carried out for determining I(plateau). It is clearly visible that the contrast parameter K decreases with increasing angle α, which is a sign for a more uniform intensity distribution.

Figure 6:
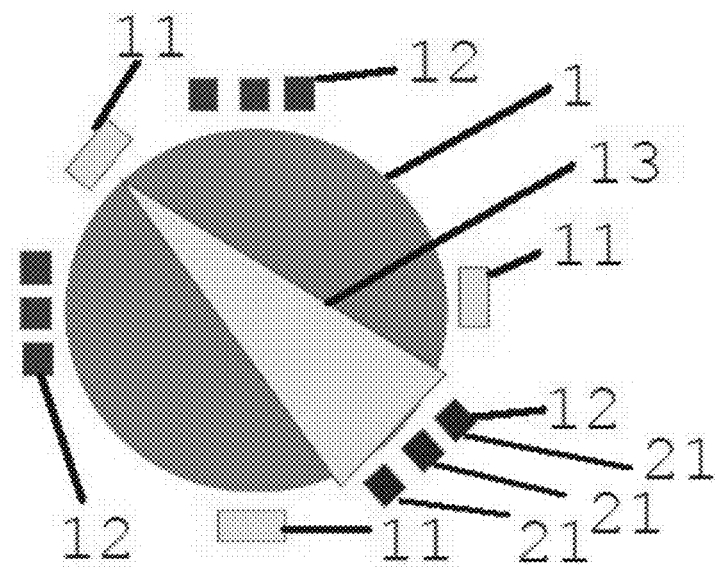
FIG. 6 shows a top view of the ATR-spectrometer according to an exemplary embodiment of the invention.

In the exemplary embodiment according to FIG. 6, the detector 12 includes a plurality of sensors 21 that are configured to detect the radiation emitted by a single one of the emitters 11. For example, it is possible in this exemplary embodiment to carry out a calibration for only one of the sensors 21 and to apply the so obtained calibration curve on the other sensors 21 of the detector.

The ATR-spectrometer 17 according to FIG. 6 includes a plurality of arrangements out of the emitter 11, the detector 12 and the wavelength selective element 18, wherein the arrangements are arranged next to each other in circumferential direction of the ATR-crystal 1, the emitters 11 are in particular configured to emit different spectra and the wavelength selective elements 18 are in particular configured to select different wavelengths. The emitters 11 and the detectors 12 are arranged alternatingly in the circumferential direction of the ATR-crystal 1.

It is understood that the foregoing description is that of the exemplary embodiments of the invention and that various changes and modifications may be made thereto without departing from the spirit and scope of the invention as defined in the appended claims.

LIST OF REFERENCE NUMERALS

1 ATR-crystal
2 cylindrical section
3 truncated conical section
4 first circular surface of the cylindrical section 2
5 second circular surface of the cylindrical section 2
6 in-coupling region
7 spatial region
11 emitter
12 detector
13 electromagnetic radiation
14 top surface of the truncated conical section 3
15 base surface of the truncated conical section 3
16 lateral surface of the truncated conical section 3
17 ATR-spectrometer
18 wavelength selective element
19 plateau
20 cone axis
21 sensor
22 first intensity distribution
23 second intensity distribution
24 intensity maximum
25 intensity minimum
26 center point
d ring width
b extension of the light emitting region
D extension of the base surface 15
α angle

What is claimed is:

1. An ATR-spectrometer comprising:
an ATR-crystal including a truncated conical section and two planar surfaces arranged in parallel to each other, the truncated conical section having a lateral surface configured to reflect an electromagnetic radiation to one of the two planar surfaces to permit the electromagnetic radiation to propagate in the ATR-crystal by a plurality of reflections on the two planar surfaces and to be subsequently coupled out of the ATR-crystal by a reflection on the lateral surface of the truncated conical section, the one of the two planar surfaces including an in-coupling region configured to couple in the electromagnetic radiation, and the in-coupling region being a projection of a circumferentially extending section of the lateral surface to the one of the two planar surfaces;
an emitter configured to emit the electromagnetic radiation via one of the two planar surfaces and essentially perpendicular to the one of the two planar surfaces to the lateral surface of the truncated conical section, the emitter having an electromagnetic radiation emitting surface, and the electromagnetic radiation emitting surface having a projection on the in-coupling region exceeding, seen from a center point of the one of the two planar surfaces, an angle of at least 1.5°; and
a detector configured to detect the electromagnetic radiation coupled out of the ATR-crystal.

2. The ATR-spectrometer according to claim 1, wherein the projection of the electromagnetic radiation emitting surface on the in-coupling region exceeds the angle of at least 8°.

3. The ATR-spectrometer according to claim 1, wherein:
the truncated conical section includes a base surface,
the emitter is configured to illuminate a region of the base surface of the truncated conical section, and
the region of the base surface has an extension in a circumferential direction of the ATR-crystal, which is longer than the extension of an electromagnetic radiation emitting region of the emitter in the circumferential direction of the ATR-crystal.

4. The ATR-spectrometer according to claim 3, wherein an extension of the base surface of the truncated conical section in a direction in which the electromagnetic radiation propagates in the ATR-crystal is at least 2.5 cm, in particular at least 4 cm.

5. The ATR-spectrometer according to claim 3, wherein an extension of the base surface of the truncated conical section in a direction in which the electromagnetic radiation propagates in the ATR-crystal is at least 4 cm.

6. The ATR-spectrometer according to claim 3, wherein the lateral surface and the base surface of the truncated conical section enclose the angle from 15° to 60°.

7. The ATR-spectrometer according to claim 3, wherein:
the truncated conical section includes a top surface,
the ATR-crystal includes a cylindrical section having two circular surfaces,
the two circular surfaces of the cylindrical section have a same diameter as the base surface of the truncated conical section, and
the base surface of the truncated conical section coincides with one of the two circular surfaces of the cylindrical section to permit the other of the two circular surfaces of the cylindrical section and the top surface of the truncated conical section to form two parallel surfaces.

8. The ATR-spectrometer according to claim 1, wherein the emitter is configured to emit the electromagnetic radiation with a divergence angle from 90° to substantially 180°.

9. The ATR-spectrometer according to claim 1, wherein the emitter is configured to emit the electromagnetic radiation with a divergence angle from 150° to substantially 180°.

10. The ATR-spectrometer according to claim 1, wherein the projection of the electromagnetic radiation emitting surface of the emitter on the in-coupling region covers at least 25% of a ring width of the in-coupling region.

11. The ATR-spectrometer according to claim 1, wherein the projection of the electromagnetic radiation emitting surface of the emitter on the in-coupling region covers 100% of a ring width of the in-coupling region.

12. The ATR-spectrometer according to claim 1, wherein the in-coupling region has a width in a radial direction of the ATR-crystal of 0.25 mm to 5 mm.

13. The ATR-spectrometer according to claim 1, wherein the emitter is arranged at a distance from the lateral surface of 0.5 mm to 7 mm.

14. The ATR-spectrometer according to claim 1, wherein the truncated conical section is truncated circular conical.

15. The ATR-spectrometer according to claim 1, wherein normals of the two planar surfaces are parallel to a cone axis of the truncated conical section.

16. The ATR-spectrometer according to claim 1, wherein the electromagnetic radiation is infrared light, the ATR-crystal is transparent for the infrared light, and the detector is configured to detect the infrared light.

17. The ATR-spectrometer according to claim 1, wherein the ATR-crystal comprises at least one of zinc sulphide, zinc selenide, germanium, calcium fluoride, barium fluoride, thallium bromide iodide, silicon, AMTIR, sapphire and diamond.

18. The ATR-spectrometer according to claim 1, further comprising:
   a wavelength selective element arranged to permit the electromagnetic radiation that is coupled out to be guided through the wavelength selective element before the electromagnetic radiation impinges on the detector,
   wherein the wavelength selective element is at least one of a prism, an optical grating, at least one of a bandpass filter and a linear variable filter, and a linear variable band pass filter and a linear variable edge filter.

19. The ATR-spectrometer according to claim 18, further comprising:
   a plurality of arrangements of emitters, detectors and wavelength selective elements arranged next to each other in a circumferential direction of the ATR-crystal, the emitters being configured to emit different spectra, the wavelength selective elements being configured to select different wavelengths, and the emitters and the detectors being arranged alternatingly in the circumferential direction of the ATR-crystal.

20. The ATR-spectrometer according to claim 1, wherein the detector comprises a plurality of sensors configured to detect radiation emitted by a single emitter.

21. The ATR-spectrometer according to claim 1, wherein:
   the detector has a photoactive surface,
   a region of the electromagnetic radiation that is coupled out of the ATR-crystal forms a plateau,
   the photoactive surface of the detector has an extension in a circumferential direction of the ATR-crystal that is shorter than an extension of the plateau, the extension of the plateau extending in the circumferential direction, and
   in the region of the electromagnetic radiation forming the plateau, an intensity distribution of the electromagnetic radiation that is coupled out of the ATR-crystal is at a maximum and substantially constant.

* * * * *